United States Patent [19]
Gensler

[11] 3,967,198
[45] June 29, 1976

[54] METHOD AND APPARATUS FOR ELECTRICALLY DETERMINING PLANT WATER STATUS

[76] Inventor: William G. Gensler, 4020 Coronodo Drive, Tucson, Ariz. 85718

[22] Filed: Sept. 20, 1974

[21] Appl. No.: 507,789

[52] U.S. Cl................................. 324/72; 324/65 R
[51] Int. Cl.² ............... G01R 19/00; G01R 27/22; G01R 15/00
[58] Field of Search ................... 324/72 R, 65 R; 73/64.3, 73

[56] References Cited
UNITED STATES PATENTS

| | | | |
|---|---|---|---|
| 2,298,506 | 10/1947 | Parker | 324/65 R |
| 2,468,972 | 5/1969 | Hagerty | 324/65 R |
| 3,005,154 | 10/1961 | Moore et al. | 324/65 R |

OTHER PUBLICATIONS

Fensom, D. S. "The Bio-Electric Potentials of Plants and Their Functional Significance" Can. J. Botany vol. 36, 1958 pp. 367–383.

Black et al., "Electrical Stimulation & its Effects on Growth & Ion Accumulation in Tomato Plants", Can. Jr. of Botany, 1971, pp. 1809–1815.

*Primary Examiner*—John K. Corbin
*Assistant Examiner*—Wm. H. Punter
*Attorney, Agent, or Firm*—Mason, Kolehmainen, Rathburn & Wyss

[57] ABSTRACT

Method and apparatus for measuring the water status of a plant by measuring the long term variations in biological electrical potential developed by the plant. The electrical potential developed by the plant is measured by placing a first electrical probe in the root environment of the plant and a second electrical probe in the body of the plant and measuring the electrical potential between the probes with an electrometer or a high impedance voltmeter. The measured potential is amplified and displayed to provide an indication of the combined water status of the plant and its root environment. Several plants or several points on a single plant may be monitored over a period of time ranging from a few days to several months by utilizing a plurality of probes and sequentially measuring the potential developed between predetermined various ones of the probes.

14 Claims, 5 Drawing Figures

METHOD AND APPARATUS FOR ELECTRICALLY DETERMINING PLANT WATER STATUS

BACKGROUND OF THE INVENTION

A. Field of the Invention

This invention relates generally to botanical measuring systems, and more particularly to a method and apparatus for electrically measuring the combined water status of a plant and its root environment by measuring the long term variations of the direct current electrical potential biologically developed between a point on the body of the plant and its root environment.

B. Prior Art

Prior art techniques for measuring the water status of a plant and its root environment consist essentially of physically measuring two parameters, namely, water potential and water content. The water potential is the chemical potential of the water in a predefined system, and is defined as the partial derivative of the Gibbs free energy of the system with respect to a change in the molar concentration of water in the system. The water potential that is measured by prior art methods is displayed as a change in the water potential with respect to a predefined reference.

The water potential arises from three physical sources. It is a measure of the change in energy per mole of water caused by solutes in the system, the energy arising from the interaction at a phase interface between solids and the water in the system, and the energy arising when the system is pressurized above ambient pressure.

The second component of the water status of a plant and its environment is simply water content which may be measured by weighing a soil sample, heating the sample to drive off the water, and then weighing the sample again.

Both of the above measurements for determining water status are purely physical measurements which may be damaging to the plant, and which are very time consuming. Furthermore, they do not assess the water continuum which exits between the root environment and the plant structure itself. Accordingly, it is desirable to provide a relatively simple method for electrically measuring the combined water status of a plant and its root environment. Such a technique would eliminate the need for making two separate distinct physical measurements and would provide a direct indication of the combined water status.

Electrical measuring devices have been used to measure the resistance of plants. Such devices generally impress an electrical potential on the plant or soil and measure the resulting current flow to obtain an indication of the conductivity. The physiological changes resulting from the impressed potential are also observed. The propagation of short term action potentials along the stems of plants has also been studied. One such study is described in Barbara G. Pickard, "Action Potentials In Higher Plants", Botanical Review, Vol. 39, No. 2, April-June 1973. The above mentioned article describes the use of electrical techniques for measuring short term variations in action potentials between points on a stem in response to external stimuli, but does not contemplate the measurement of slowly varying changes in potential between the root environment and a point on the body of a plant to provide an indication of the combined water status of the plant and its root environment.

SUMMARY OF THE INVENTION

It is an object of the present invention to provide a method and apparatus for electrically measuring the combined water status of a plant and its root environment.

It is another object of the present invention to provide a method and apparatus for monitoring the changes in biological electric potential of a plant that relate to water status.

It is a further object of the present invention to provide a system that monitors and records the water status of a plant in response to changes in the physical environment of the plant.

It is yet another object of the present invention to provide a method and apparatus for monitoring the water status of a plurality of plants and a plurality of points on each plant.

In a preferred embodiment of the invention, a first electrical probe is placed in the root environment of the plant and a second probe is placed in the body of the plant. The root environment may comprise soil or a hydroponic solution, and the probes may be fabricated from any relatively chemically inert material such as platinum, stainless steel or carbon. It is also possible to measure the potential with stable yet chemically active probes, but presently such probes are expensive and tend to wear out quickly.

The electrical potential biologically generated by the plant is measured by means of an electrometer or a high impedance voltmeter. Changes in the values of the potential thus measured are monitored over long time periods ranging from days to months and displayed to provide an indication of the combined water status of the plant. Optionally, apparatus may be provided for plotting the measured values to provide a record of the changes in the combined water status as a function of time and the physical environment of the plant.

The invention, both to its organization and method of operation, together with further objects and advantages thereof, will best be understood by reference to the following specification taken in conjunction with the accompanying drawings in which.

DETAILED DESCRIPTION

Figure 1:
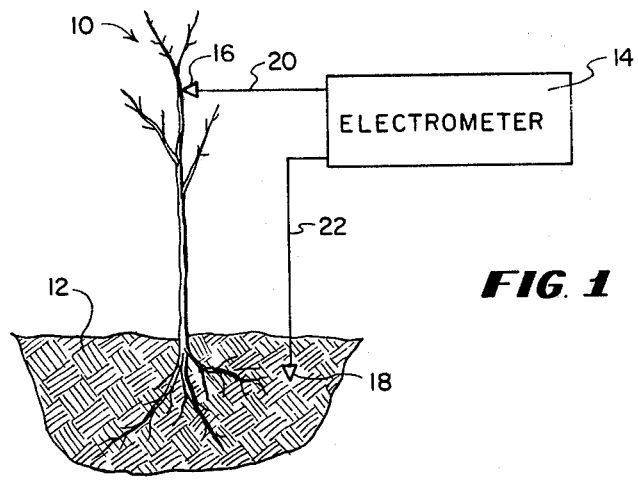
FIG. 1 is a simplified block diagram illustrating the basic principles of the method and apparatus according to the invention for measuring the combined water status of a plant and its root environment.

Referring now to the drawings, FIG. 1 illustrates the basic operating principles of the method and apparatus for measuring the combined water status of a plant and its root environment. In FIG. 1, there is shown a plant 10 growing in a root environment 12. The plant 10 is any plant whose water status is to be measured. The water status of tomato, cotton and coleus plants has been successfully measured using the method and apparatus of the present invention. The root environment 12 may be conventional soil or a hydroponic nutrient solution.

An electrometer 14 is connected to a portion of the body of the plant 10 and to the root environment 12 by means of a pair of probes 16 and 18 and a pair of flexible wire leads 20 and 22. The probe 16 is a probe of the type that penetrates the body of the plant rather than a surface probe. A penetrating type probe has several advantages over a surface probe. Among these are the relative permanence with which a penetrating type probe may be implanted in the body of the plant. At the present time, no material has been found that will readily adhere to the surface of a plant for any extended period of time without drying out, peeling off or causing surface changes to the tissue of the plant. Because the outer surface or cuticle of a plant is relatively nonconducting, electrical contact to the surface of a plant is relatively difficult. The permanence with which a penetrating probe can be attached to a plant makes it usable under field conditions where a surface probe would be unsuitable.

Several different types of penetrating probes have been used in implementing the invention, including conductively sheathed and unsheathed probes. Any relatively stable material such as platinum, stainless steel and carbon may be used as the conductive material of the probe, and any stable insulator such as the plastic material sold under the trademark TEFLON may be used to sheath the probes. The advantage of using sheathed probes is that a sheathed probe does not short circuit various portions of the plant tissue together as does an unsheathed probe. However, satisfactory results have been obtained with unsheathed probes fabricated from 0.01 inch diameter stainless steel wire. The advantage of unsheathed stainless steel probes is their low cost and ease of cleaning.

Connection to the implanted probe 16 is made by forming a one millimeter loop in the probe 16 and passing the conductor 20 through the loop. An electrical connection is made by coating the junction of the wire 20 and the probe 16 with conductive silver paint. The wire 20 may be taped to the body of the plant to provide support, and the junction formed by the one millimeter loop provides a flexing action to minimize the movement of the probe 16 within the body of the plant 10.

The electrometer 14 may be a conventional electrometer or a high impedance voltmeter having an imput impedance of at least $10^9$ ohms. The amount of power drawn from the plant is determined by the input impedance of the electrometer, and it has been determined experimentally that reducing the input impedance of the electrometer 14 to a value below $10^9$ ohms renders the measured potential highly sensitive to the input impedance. When the input impedance is maintained above $10^9$ ohms, the measured potential is substantially unaffected by variations in the input impedance of the electrometer. It has also been found advantageous to utilize a battery operated electrometer as the electrometer 14 because electrostatic charge transfer into the plant can result in spurious readings when line driven equipment is used.

Figure 2:
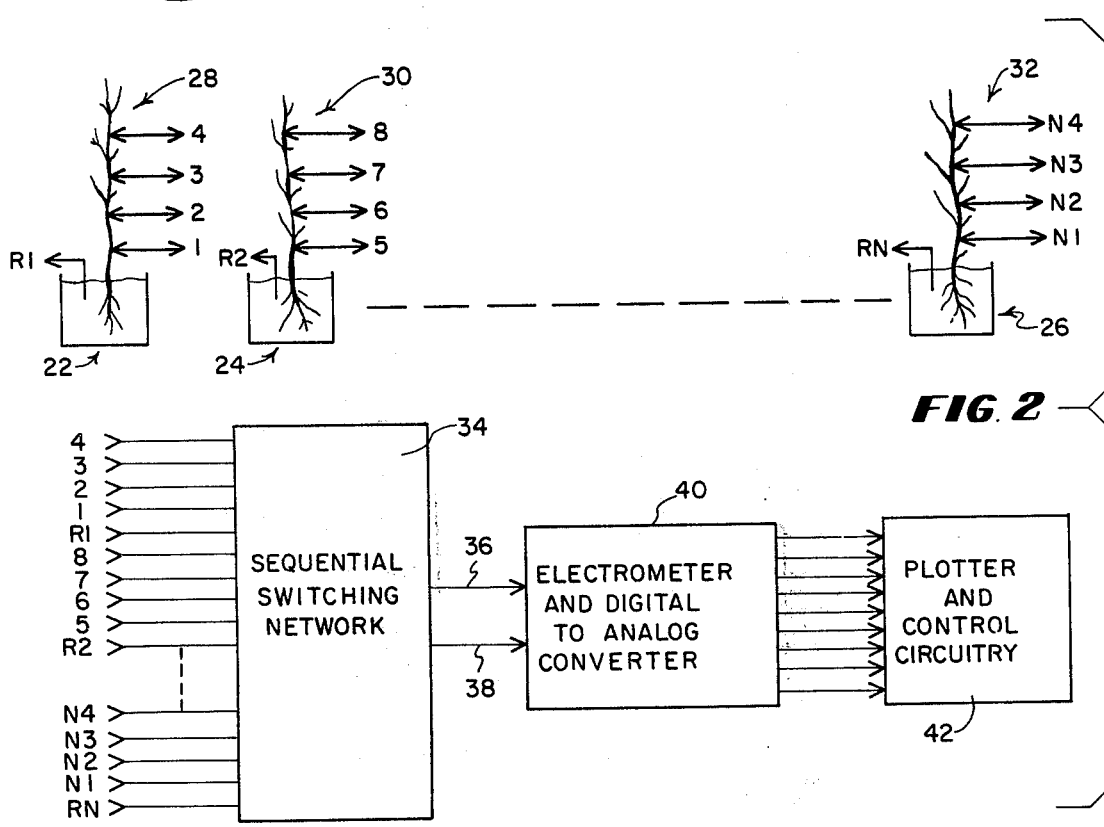
FIG. 2 is a block diagram of apparatus suitable for monitoring the water status of a plurality of plants utilizing the principles of the present invention.

In order to determine the variations in water status between different plants and between different portions of a single plant, the apparatus shown in FIG. 2 was constructed. The apparatus of FIG. 2 is capable of monitoring the water status of N different plants at four different points on each of the N plants. In FIG. 2, there is shown a plurality of containers 22, 24 and 26, each containing a respective plant 28, 30 and 32. Any number of plants may be monitored, and in one experimental embodiment six plants have been simultaneously monitored. Each of the plants 28, 30 and 32 has four probes similar to the probe 16 discussed in conjunction with FIG. 1 implanted therein. The output leads of the probe implanted in the plants 28, 30 and 32 are designated as 1, 2, 3 and 4; 5, 6, 7 and 8; and N1, N2, N3 and N4, respectively. Each of the containers 22, 24 and 26 has a root environment comprising soil or a hydroponic nutrient solution contained therein. A reference probe is inserted into the root environment in each container, and output leads R1, R2 and RN are connected to the respective reference probes inserted in the containers 22, 24 and 26.

Each of the probes implanted in the plants 28, 30 and 32, and each of the reference probes R1, R2 and RN is connected to an input of a sequential switching network 34. The inputs of the sequential switching netword 34 are numbered to correspond with the designations of the respective output leads from the implanted and reference probes connected thereto. The sequential switching network sequentially switches one of the leads from one of the reference probes and one of the leads from one of the implanted probes to a pair of output leads 36 and 38. The output leads 36 and 38 are connected to an electronic circuit 40 containing an electrometer and a digital to analog converter. The electronic circuit 40 has eight output leads which apply the measured potential to a plotter circuit 42 in digital form.

Figure 3:
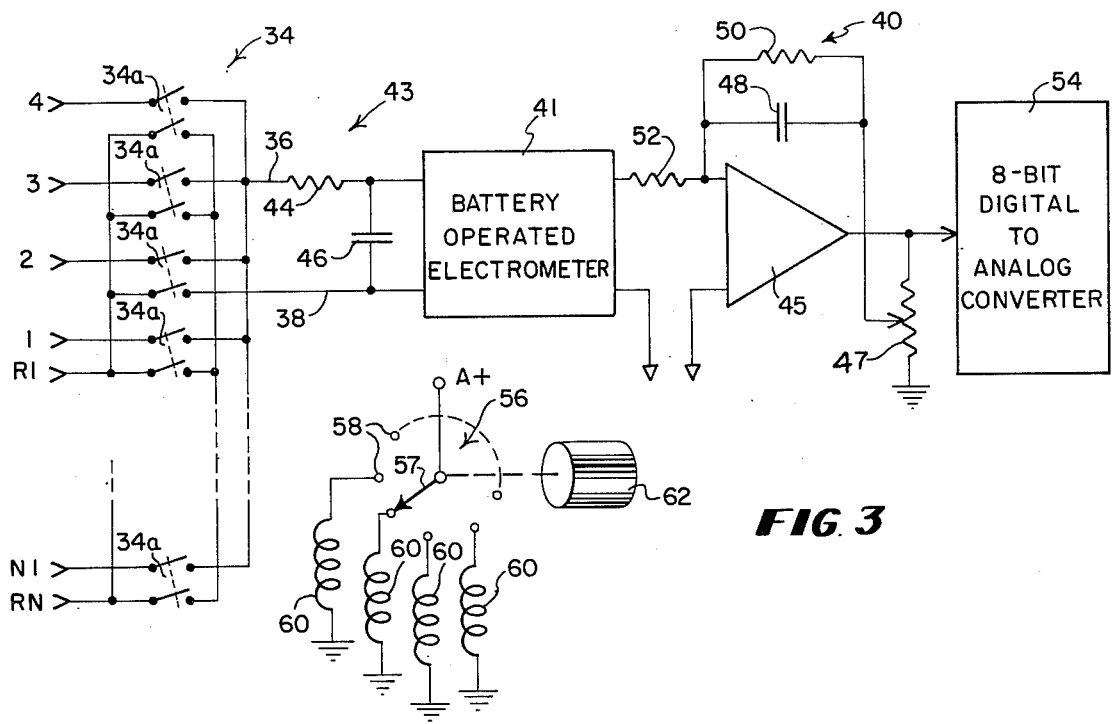
FIG. 3 is a more detailed block diagram of the sequential switching network and the electrometer and digital to analog converter of FIG. 2.

FIG. 3 shows the sequential switching network 34 and the electronic circuit 40 in greater detail. In the embodiment shown in FIG. 3, the sequential switching network contains a plurality of double pole switches 34a that sequentially connect one of the reference probes and one of the implanted probes to a battery operated electrometer 41. A low pass filtering network 43 comprising a resistor 44 and a capacitor 46 is interposed between the sequential switching network 34 and the battery operated electrometer 41. The filtering network 43 serves to low pass filter the signal obtained from the output of the switching network 34 and to apply the filtered signal to the battery operated electrometer. The filtering circuit 43 serves to filter out the short term variations in the electric potential provided by the plant and also serves to filter out spurious noise components. As a result, only the slowly varying potential resulting from a change in the combined water status of the plant and root environment are applied to the electrometer 41.

The output of the electrometer 41 is connected to a pair of inputs of an operational amplifier 45. The operational amplifier 45 may be a conventional operational amplifier available from a variety of electronic components manufacturers. A feedback network comprising a potentiometer 47, a capacitor 48 and a resistor 50 is connected between the output and an input of the operational amplifier 45 to set the gain and the frequency characteristics of the amplifier. The potentiometer 47 serves to set the gain of the amplifier 45. An input resistor 52 is interposed between the electrometer 41 and the operational amplifier 45.

The output signal from the amplifier 45 is an analog voltage that is an amplified facsimilie of the output signal from the battery operated electrometer 41. The output signal from the operational amplifier 45 is applied to the input of an eight-bit digital to analog converter 54. The digital to analog converter 54 converts the analog signal from the amplifier 45 to one of a series of 256 discrete digital signals, and applies the digital signals to eight output leads which are connected to the plotter 42 of FIG. 2. The plotter 42 is responsive to the signals from the converter 54 and plots a discrete point for each of the 256 combinations of signals applied to the eight leads. If desired, a paper tape punch may be employed in conjunction with the plotter 42 to store the digital information from the converter 54 prior to the plotting of the information onto graph paper. The digital-analog system described above provides one way to measure and plot the electrical potential of a plant, but it should be noted that a completely analog system, or a system employing other combinations of digital and analog apparatus may also be used.

In the sequential switching network 34 shown in FIG. 3, each of the double pole switches 34a forms a part of an electromagnetic relay. In the embodiment shown, the relays are selectively energized by means of a rotating switch 56 having a rotating arm 57 connected to a source of direct current potential and a plurality of contacts 58 each connected to an energizing winding 60 of one of the double pole relays. The rotating switch 56 may be driven by an electric motor 62 to sequentially energize the windings 60 to sequentially close the double switches 34a. The above mentioned action sequentially connects each one of the implanted probes and a corresponding reference probe to the electrometer 41. The details of the sequential switching network 34 described above are intended only to illustrate the principle of sequentially connecting the probes to the electrometer 41, and any sequential switching network including electronic switching networks and other types of electromechanical switching networks may be used.

The switching network 34 samples each pair of probes at 12 minute intervals, and experimental data has shown that potential variations resulting from changes in water status do not occur during time intervals appreciably shorter than 12 minutes. Therefore, although a faster sampling rate may be employed, the 12 minute sampling rate of the present embodiment has been proven satisfactory in a practical system.

Figure 4:
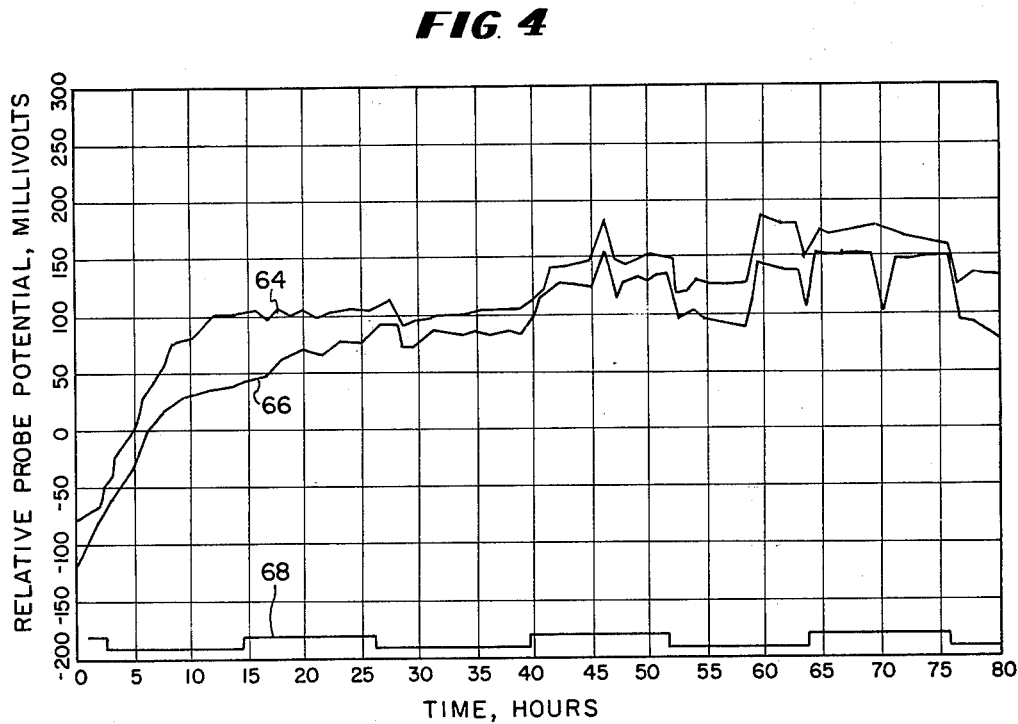
FIG. 4 is a graph showing the biologically generated electrical potential of a plant as measured by the method and apparatus according to the invention displayed as a function of time and the illumination applied to the plant.

FIG. 4 shows a plot of experimental data obtained by the method and apparatus of the present invention, and shows the effects of wound healing and photoperiodicity. The graph of FIG. 4 is included to show that the variation in the electrical potential along the stem of a plant can arise as a result of various stimuli, and that care must be taken to assure that the potential being measured gives a true indication of the water status.

Each of the curves 64 and 66 represents a variation in the potential of the probes implanted at two points along the stem of the plant with respect to the potential of a probe implanted in the root environment. When the probes are first implanted into the plant, the potential measured at each of the implanted probes is negative with respect to the probe implanted in the root environment. As the wound caused by the implanting process heals, the potential at the implanted probes slowly rises and stabilizes at a positive value.

The plant whose response is depicted in FIG. 4 was exposed to alternating periods of lightness and darkness as indicated by the curve 68 near the bottom of the graph. A rise in the curve 68 denotes a period of lightness, and a drop indicates a dark period. The light and dark periods affect the measured potential as reflected by the fluctuations in the curves 64 and 66 which follow the periodicity of the illumination curve 68.

The curves 64 and 66 depicting the potential at two locations on the stem of the plant show rather close correlation to the illumination curve 68, but no correlation has been observed between potential and the location of the probe on the stem. Experimentation has shown that the measured potential usually starts at a negative value and rises to a positive value as the wound heals independently of the position of the probes, provided that the probes are implanted in the stem in an area above the root and the reference probe is implanted in the root environment. When the reference probe is inserted at the base of the stem near the root zone, or in the stem, the potentials are no longer consistently positive. This indicates that the potential being measured reflects the water status of both the plant and the root environment.

Figure 5:
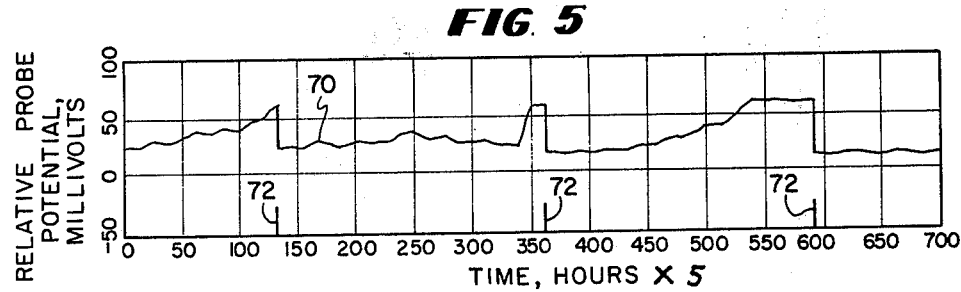
FIG. 5 is a graph showing the variations in the potential developed by a plant resulting from the addition of water to the root environment.

FIG. 5 shows a plot of experimental data of the change in the water status of a plant in response to the addition of water to the root environment. The plant was monitored for a period of time in excess of several hundred hours to minimize the effects of extraneous stimuli. Data points were taken at 12 minute intervals and the numbers below the horizontal axis of FIG. 5 represent the data point numbers. These numbers may be converted to hours by dividing by five. The graph of FIG. 5 was obtained by measuring the electrical potential at a point on the stem of a cotton plant growing in a soil root environment with respect to the potential of a probe inserted in the soil. The curve 70 represents the potential measured at a probe inserted into the stem of the plant, and the vertical lines 72 represent the addition of water to the soil. The curve 70 exhibits a sharp drop whenever water is added to the root environment and a gradual rise subsequent to watering, indicating the change in the water status of the plant. The response of the cotton plant depicted in FIG. 5 shows a very rapid response to the addition of water and a generally exponential rise between waterings. The measured characteristics vary with the variety of plants being measured, and some plants have response curves characterized by relatively inactive periods separated by periods of high activity when water is added, however, all plants studied to date have exhibited a correlation between the addition of water and a change in the measured electrical potential indicating that the measurements to reflect a change in combined water status.

While there have been illustrated and described various embodiments of the present invention, it will be apparent to those skilled in the art that modifications thereof will occur to those skilled in the art. It is intended in the appended claims to cover all such changes and modifications as fall within the true scope and spirit of the present invention.

What is claimed as new and desired to be secured by Letters Patent of the United States is:

1. A method for measuring the water status of a plant comprising the steps of:
    placing a first electrical probe in contact with the root environment of the plant;

placing a second electrical probe in contact with the body of the plant;

measuring the long term variations in electrical potential generated by the plant between the first and second probes, said step of measuring the long term variations in electrical potential including the steps of sensing the electrical potential generated by the plant, filtering out the short term variations of the sensed potential, and recording the long term variations of the sensed potential; and relating the long term variations in electrical potential to the water status of the plant.

2. The method recited in claim 1 wherein the step of measuring the long term variations in electrical potential include the step of monitoring the filtered electrical potential for an extended period of time.

3. The method recited in claim 2 wherein said extended period of time ranges from days to months.

4. The method recited in claim 2 further including the step of providing a graphical indication of the filtered electrical potential.

5. The method recited in claim 4 further including the steps of placing a plurality of electrical probes in contact with the body of the plant at various locations thereon, and measuring and displaying the value of the electrical potential between said first probe and each one of the electrical probes contacting the body of the plant.

6. The method recited in claim 4 further including the steps of placing a plurality of first electrical probes in contact with the root environments of a corresponding plurality of plants, and placing a plurality of second electrical probes in contact with the bodies of said plurality of plants, and sequentially measuring and displaying the electrical potential developed between one of said first electrical probes and a corresponding one of said second electrical probes.

7. The method recited in claim 1 wherein the step of placing the second electrical probe in contact with the body of the plant includes the step of inserting the probe into the body of the plant.

8. The method recited in claim 7 wherein the step of placing the second electrical probe in contact with the stem of the plant comprises the step of inserting the probe into the stem of the plant.

9. The method recited in claim 6 wherein the step of placing the first electrical probe in contact with the root environment of the plant comprises the step of inserting the probe into the root environment.

10. Apparatus for measuring the combined water status of a plant and its root environment comprising:

first probe means for making electrical contact with the root environment;

second probe means for making electrical contact with the body of the plant;

means coupled to said first and second probe means for measuring the electrical potential generated therebetween by said plant, said measuring means having means for low pass filtering the measured electrical potential to attenuate the short term variations thereof; and means for monitoring the filtered electrical potential.

11. Apparatus as recited in claim 10 including a plurality of second probe means, and means interposed between each of said second probe means and said measuring means for selectively connecting each of said second probe means to said measuring means.

12. Apparatus as recited in claim 11 further including a plurality of first probe means, and means interposed between each of said first probe means and said measuring means for selectively connecting each one of said first probe means to said measuring means.

13. Apparatus as recited in claim 12 further including means connected to said selective connecting means for connecting predetermined ones of said first and second probe means to said measuring means in a predetermined sequence, said measuring means including means for recording the values of the electrical potential measured thereby.

14. Apparatus as recited in claim 10 wherein said measuring means has an input impedance of at least $10^9$ ohms.

* * * * *